United States Patent [19]

Bringhurst et al.

[11] Patent Number: Plant 5,264

[45] Date of Patent: Jul. 31, 1984

[54] STRAWBERRY PLANT 'SOQUEL'

[75] Inventors: Royce S. Bringhurst, Davis; Victor Voth, Santa Ana, both of Calif.

[73] Assignee: The Regents of the University of California, Berkeley, Calif.

[21] Appl. No.: 452,694

[22] Filed: Dec. 23, 1982

[51] Int. Cl.[3] ..... A01H 5/03

[52] U.S. Cl. ..... Plt./48

[58] Field of Search ..... Plt./48

*Primary Examiner*—Bagwill Robert E.

*Attorney, Agent, or Firm*—Townsend & Townsend

[57] ABSTRACT

A new and distinct variety of strawberry plant of the short-day type characterized by its suitability for winter and summer plantings and its runner prolificy in the nursery. The variety is further characterized by its fruiting habit which is earlier and longer than 'Aiko'. The plants of the variety are low to semi-erect and its flowers are self fertile. The fruit is medium conic to very symmetrical in shape, often hollow internally and firm and durable making it suitable for the fresh market and processing. Fruit skin has a finish more glossy and attractive than 'Aiko' and fruit flavor is comparable to that of the best California varieties presently in use.

3 Drawing Figures

DESCRIPTION

This invention relates to a new and distinctive short-day type strawberry cultivar designated as 'Soquel' which is the result of a cross of 'Cruz' U.S. Plant Pat. No. 3,979) × 'Aiko' (U.S. Plant Pat. No. 3,981) made in 1977.

'Soquel' first fruited at the University of California Wolfskill Experimental Orchards near Davis in 1974 where it was selected and designated originally as Cal 72.330-107. It was tested later as advanced selection C95.

'Soquel' has been propagated asexually by runners and has been tested at various University of California field stations and facilities and to a very limited extent in a few growers' fields under Test Agreement.

Figure 1:
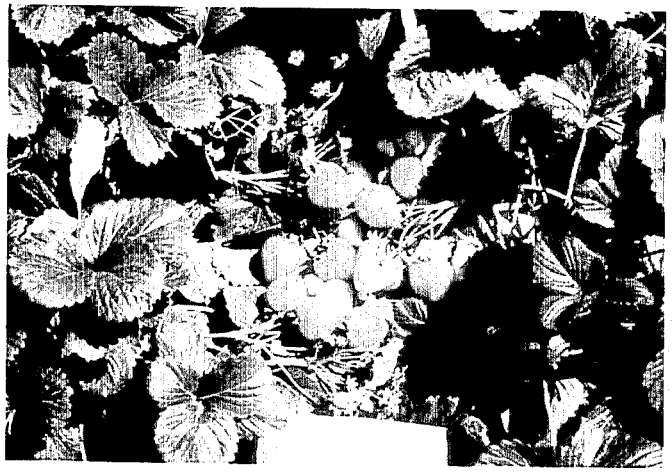
FIG. 1 shows fall fruiting characteristics of the plant (Oct. 4, 1982).
Figure 2:
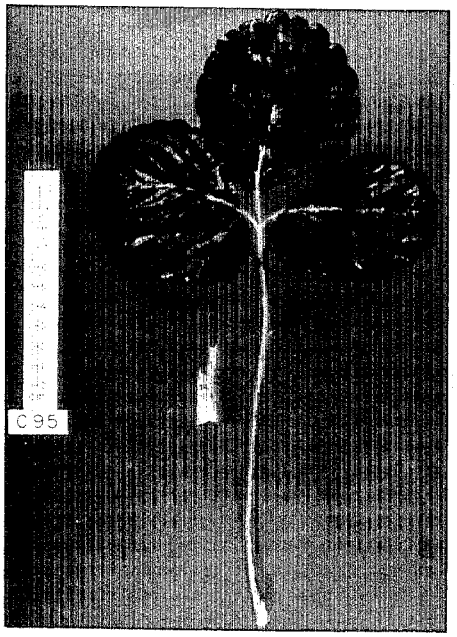
FIG. 2 shows a typical midsummer mature leaf from a plant in full fruit.
Figure 3:
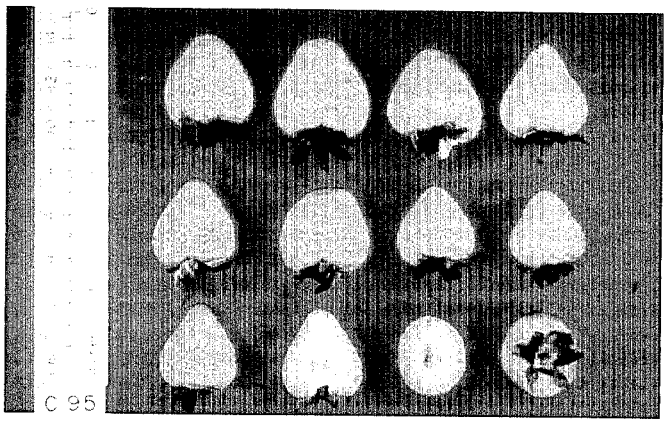
FIG. 3 shows representative early-season fruit with longitudinal and cross-sectional views.

'Soquel' is earlier fruiting than 'Aiko' but it persists in fruiting about as long. 'Soquel' has performed well in winter and summer planting experiments particularly in central coastal California.

PLANTS AND FOLIAGE

'Soquel' plants are low to semi-erect in growth habit, slightly larger than those of 'Aiko' which it resembles closely but smaller than those of the standard 'Tioga' in both winter and summer plantings as as estimated by measuring petiole length on plants in full fruit. Leaflets of 'Soquel' are larger than those of 'Aiko' but smaller than those of 'Tioga' averaging about the same number of serrations per terminal half leaf. 'Soquel' leaves are less elongate (L/W index equals about 1.09) and more rugose than those of 'Aiko' (L/W index=about 1.22). Leaves of 'Soquel' are about the same color and intensity as those of 'Aiko', 7.5GY4/4 (Munsell Color System-Nickerson Color Fan). Runner production in nursery plantings is excellent, better than 'Tioga'.

ISOZYMES IN LEAF EXTRACTS

'Soquel' has been classified for three enzyme systems: (A) Phosphoglucoisomerase (PGI); (B) Leucine amono peptidase (LAP); and (C) Phosphoglucomutase (PGM); identical to 'Cruz' and 'Aiko' for PGI and LAP, but unique among all cultivars and selections we have tested for PGM.

| | 'Tioga' | 'Tufts' | 'Doug-las' | 'Cruz' | 'Aiko' | 'Pa-jaro' | 'Soquel' |
|---|---|---|---|---|---|---|---|
| PGI | A1 | A2 | A3 | A3 | A4 | A4 | A4 |
| LAP | B1 | B3 | B3 | B3 | B3 | B3 | B3 |
| PGM | C3 | C4 | C1 | C1 | C2 | C1 | C6** |

*1981 J. Amer. Soc. Hort. Sci. 106:684–687.

**Novel Type.

FLOWERING AND FRUITING

'Soquel' flowers are borne on medium long, semi-erect peduncles which are brought down quickly by the weight of the fruit. The flowers are self fertile with ample pollen throughout the season and consequently there is little malformed fruit.

FRUIT APPEARANCE

'Soquel' fruit is medium conic and generally very symmetrical. Internally the fruit is often hollow. The fruit skin color is about 7.5R5/13 (ibid), about the same color as that of fully colored 'Aiko' but the finish is more glossy and attractive. The flesh is somewhat lighter than the skin particularly during the early part of the season. The achenes are bright yellow positioned about flush with surface in contrast to those of 'Aiko' which tend to be slightly embedded. The calyx is medium to large in size, borne about flush on the base of the fruit. The fruit is at least as firm and durable as that of 'Tioga', 'Tufts' or 'Aiko' according to penetrometer readings and handling comparisons. The fruit size averages larger than that of 'Tioga' or 'Aiko' with a wide range in size as the season advances.

FRUIT QUALITY

'Soquel' has averaged higher ascorbic acid content (51 mg/100 g fresh fruit) than 'Tioga' (26), 'Tufts' (30)

or 'Douglas' (32), about the same as 'Pajaro' (48) and 'Aiko' (50), as tested six times on summer and winter plantings during 1980, 1981 and 1982 by the method of Loeffler and Ponting (1942, J. Indust. and Engin. Chem. 14:846). Soluble solids readings were not significantly different from those of 'Tioga', 'Tufts', 'Douglas', 'Aiko' or 'Pajaro' from comparable plantings. The flavor of 'Soquel' is very good, comparable to that of the best flavored cultivars now used in California in our opinion and according to most who have tried it. It is suitable for fresh market and processing.

We claim:

1. The new and distinct variety of strawberry plant herein described and illustrated and identified by the characteristics enumerated above.

* * * * *

UNITED STATES PATENT AND TRADEMARK OFFICE

CERTIFICATE OF CORRECTION

PATENT NO. : Plant 5,264

DATED : July 31, 1984

INVENTOR(S) : Bringhurst, et al.

It is certified that error appears in the above-identified patent and that said Letters Patent is herebv corrected as shown below:

Column 2, line 15, in the subcolumn corresponding to the cultivar Cruz, delete "C1" and substitute --C2--.

Signed and Sealed this

Thirty-first Day of March, 1992

*Attest:*

HARRY F. MANBECK, JR.

*Attesting Officer*

*Commissioner of Patents and Trademarks*